United States Patent [19]
Tubergen

[11] Patent Number: 5,900,113
[45] Date of Patent: *May 4, 1999

[54] METHOD OF USING FLUORESCENT TRACERS TO MONITOR CHLORINE DIOXIDE IN PULP AND PAPER PROCESSES

[75] Inventor: Karen R. Tubergen, Mt. Prospect, Ill.

[73] Assignee: Nalco Chemical Company, Naperville, Ill.

[ * ] Notice: This patent is subject to a terminal disclaimer.

[21] Appl. No.: 08/767,574

[22] Filed: Dec. 16, 1996

Related U.S. Application Data

[63] Continuation-in-part of application No. 08/581,413, Dec. 29, 1995, abandoned, which is a continuation-in-part of application No. 08/312,021, Sep. 26, 1994, abandoned.

[51] Int. Cl.$^6$ ........................................................ D21C 9/14
[52] U.S. Cl. ........................ 162/49; 162/67; 162/87; 436/55; 436/172
[58] Field of Search ........................ 162/198, 263, 162/49, 67, 89; 210/109, 739, 745; 422/62, 82.05, 82.08; 436/55, 27, 56, 172

[56] References Cited

U.S. PATENT DOCUMENTS

| | | | |
|---|---|---|---|
| 3,962,029 | 6/1976 | Wettermark et al. | 162/49 |
| 4,783,314 | 11/1988 | Hoots et al. | 422/3 |
| 4,992,380 | 2/1991 | Moriarty et al. | 436/55 |
| 5,166,074 | 11/1992 | Vessey et al. | 436/103 |
| 5,171,450 | 12/1992 | Hoots | 210/701 |
| 5,304,800 | 4/1994 | Hoots et al. | 250/302 |
| 5,320,967 | 6/1994 | Avallone et al. | 436/50 |
| 5,389,548 | 2/1995 | Hoots et al. | 436/6 |
| 5,411,889 | 5/1995 | Hoots et al. | 436/6 |
| 5,413,719 | 5/1995 | Sivakumar et al. | 210/708 |
| 5,702,684 | 12/1997 | McCoy et al. | 424/10.3 |

FOREIGN PATENT DOCUMENTS

| | | |
|---|---|---|
| 0365 815 | of 0000 | European Pat. Off. . |
| 0 610 860 A2 | 8/1994 | European Pat. Off. . |

*Primary Examiner*—Peter Chin
*Assistant Examiner*—Steven B. Leavitt
*Attorney, Agent, or Firm*—Margaret M. Brumm; Thomas M. Breininger

[57] ABSTRACT

The present invention provides a method of monitoring a papermaking system and unit operations contained therein to optimize the overall papermaking process. The method comprises employing a fluorescent tracer that is selectively carried through the entire papermaking system or in a specific unit operation and is sufficiently inert and sufficiently stable under the environmental and chemical conditions of the system from its addition point to the sampling point. A sample is withdrawn from the papermaking environment (either via 'grab' or on-line side stream sampling) and the withdrawn sample subjected to analysis. The analysis comprises comparing the tracer concentration to a standard to determine the concentration of tracer in the sample and/or determining the time of first appearance of said tracer from addition point to the sampling point and/or subsequent decay of said tracer concentration at the sampling point. Finally, from this information process variables are adjusted to ensure stable paper machine operations and a high standard of paper quality.

1 Claim, 6 Drawing Sheets

REFINED KRAFT CHEST

REFINED KRAFT CHEST
SLUG FEED

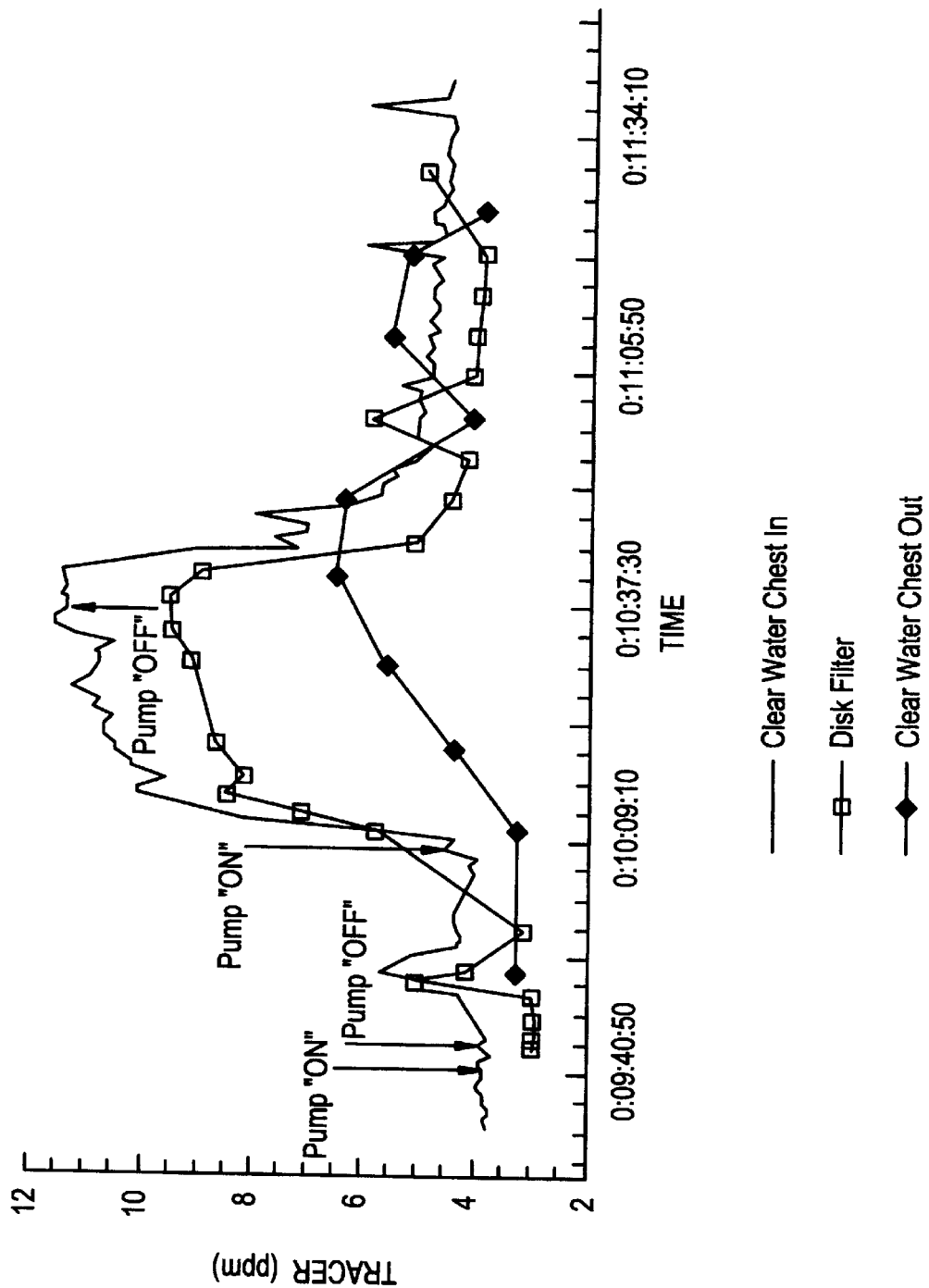

5,900,113

METHOD OF USING FLUORESCENT TRACERS TO MONITOR CHLORINE DIOXIDE IN PULP AND PAPER PROCESSES

REFERENCE TO RELATED PATENT

The present application is a continuation-in-part of application Ser. No. 08/581,413 filed Dec. 29, 1995, now abandoned, by Karen R. Tubergen, entitled "Fluorescent Tracer for Diagnostic Use in Pulp and Paper Processes", which is, in turn, a continuation-in-part of application Ser. No. 08/312,021 filed Sep. 26, 1994, now abandoned, by Karen R. Tubergen, entitled "Fluorescent Tracer for Diagnostic Use in Pulp and Paper Processes", the disclosures of which are incorporated herein by reference.

FIELD OF THE INVENTION

The present invention is in the technical field of diagnostic methods and agents for use in paper and paperboard generating systems.

DESCRIPTION OF THE PRIOR ART

The production of paper and paperboard materials involves a complex use of fibrous raw materials (pulp), non-fibrous components (additives), and water. The flow of pulp through a paper mill system runs through a variety of mechanical unit operations such as screens, cleaners, thickeners, storage chests, etc. The efficiency of each of these steps contributes to the overall productivity and quality of the final paper/paperboard product. The primary concern is to produce a uniform papermaking furnish to ensure stable paper machine operation and a high standard of paper quality.

Because of the dynamics of a papermaking process, the controlled addition and monitoring of process treatment chemicals, such as biocides, dispersants, felt cleaners and retention and drainage aids, is typically a difficult task and inexact science. Changes in system flow rates, paper grade and production changes, etc., result in a continually changing demand for these chemicals. In a papermaking system to which a treating chemical is added, maintaining the proper feed level of the component is essential for optimal performance. Improper feed rate of treating component can lead to serious problems. For example, synthetic polymeric coagulants and flocculants are extensively used as retention aids in the papermaking process. They are added not only to retain various furnish components and additives, but also to improve dewatering and sheet formation. If improper levels of retention aids are fed, unretained materials build up in the white water system and contribute to deposit problems on the machine which results in lost or slowed production and poor quality.

Unfortunately, quick and accurate on-site testing for the actual concentrations of these different chemicals is often impractical, generally requiring sophisticated analytical techniques. Routine off-site testing, if a method is available, is typically too expensive and may require weeks to receive the results. In addition, accurate information from the mill regarding mixing efficiency, channelling, residence times, flow rates, contamination and other pertinent information necessary to optimize a chemical program is not always available. It is the intent of this invention to demonstrate the use of fluorescent tracing materials as diagnostic agents with respect to mill system parameters and unit operations. With in-depth knowledge of said parameters and operations, the efficient and effective use of process additives is greatly enhanced.

The use of fluorescent tracers in cooling water and boiler systems has been practiced for some years. U.S. Pat. Nos. 4,783,314 (Hoots and Hunt); 5,304,800 (Hoots, et.al.); 5,282,379 (Harder, Pierce, and Post); 5,320,097 (Avallone, et.al.) the disclosures of which are hereinafter incorporated by reference presents examples of the uses of fluorescent tracers in said systems. However, there are distinct and undeniable differences in the matrices of cooling water and boiler systems in comparison to that of a paper process system. The former systems are in what might be referred to as "clean" matrices, wherein the total solids, turbidity, and color are orders of magnitude less than those encountered in paper process streams. In the production of paper, the total solids present in the process stream varies widely depending on the sampling point within the papermaking system. For example, "high con" pulpers have furnish consistencies as high as 12%. In contrast, with an efficient dissolved air flotation clarifier, effluents from such a unit process afford total solids of less than 0.01% (100 ppm).

SUMMARY OF THE INVENTION

The present invention provides a method of monitoring a papermaking system and unit operations contained therein to optimize the overall papermaking process. The method comprises employing a fluorescent tracer that is selectively carried through the entire papermaking system or in a specific unit operation and is sufficiently inert and sufficiently stable under the environmental and chemical conditions of the system from its addition point to the sampling point. A sample is withdrawn from the papermaking environment (either via 'grab' or on-line side stream sampling) and the withdrawn sample subjected to analysis. The analysis comprises comparing the tracer concentration to a standard to determine the concentration of tracer in the sample and/or determining the time of first appearance of said tracer from addition point to the sampling point and/or subsequent decay of said tracer concentration at the sampling point. Finally, from this information process variables are adjusted to ensure stable paper machine operations and a high standard of paper quality.

BRIEF DESCRIPTION OF THE DRAWINGS

FIG. 7 is a plot of tracing agent fluorescence versus time at three sampling sites in a Midwestern papermill's chlorine dioxide flow loop.

DESCRIPTION OF THE PREFERRED EMBODIMENTS

Figure 1:
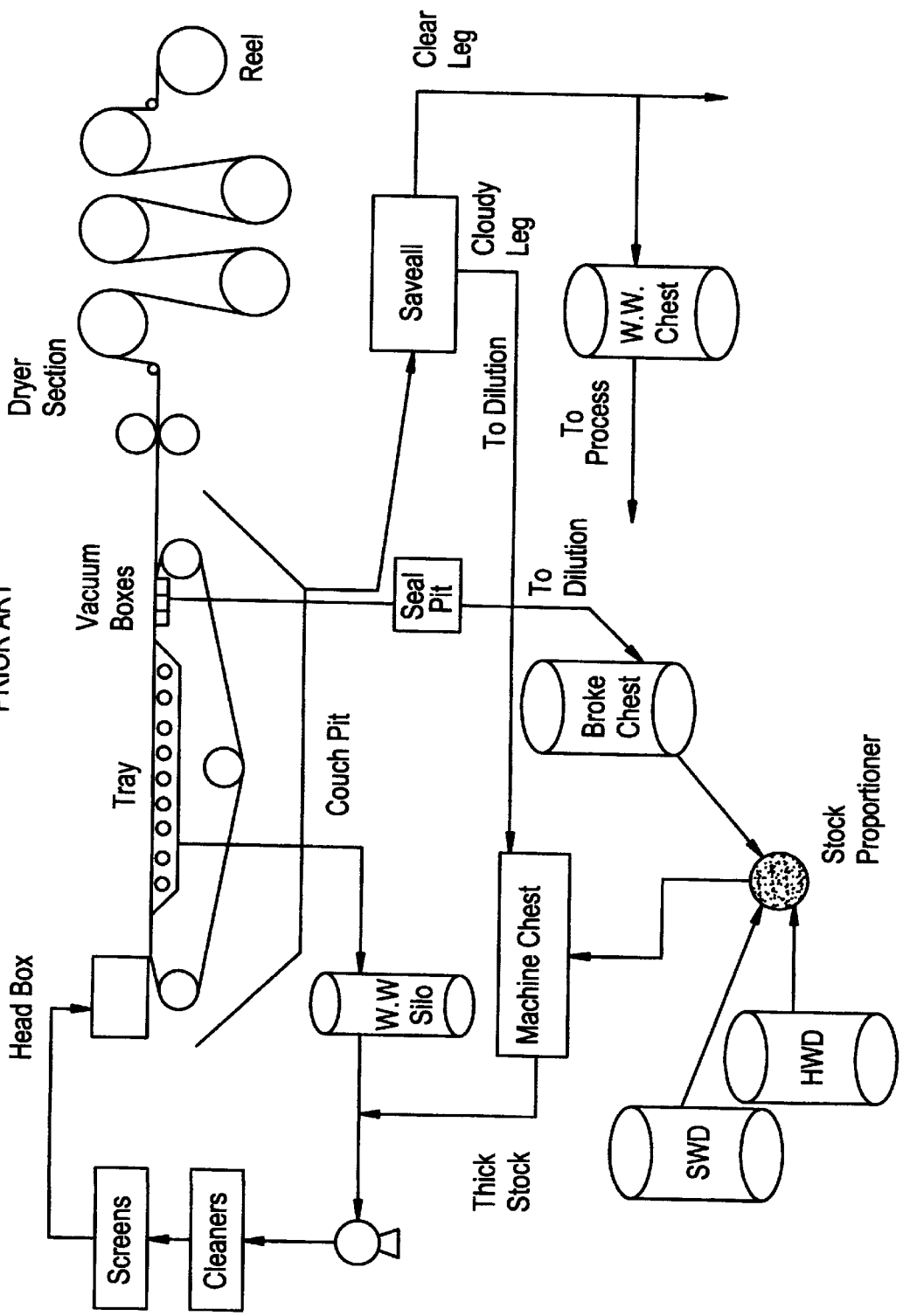
FIG. 1 is a schematic of a typical papermaking system illustrating various unit processes within the system.

One aspect of the present invention provides a method of monitoring a papermaking system using a fluorescent tracer material. The fluorescent tracing agent is added in its entirety directly to the paper system or unit operation therein, to define such system parameters as: stock chest turnover rates, water recirculation times, chest volumes, leak detection; and/or fiber ratio blends.

In an embodiment, the chemical compound(s) selected as tracer materials should be inert. That is, an inert tracer(s) should not be one that is consumed or lost to the water of the paper system, for instance due to degradation, deposition, complexation, or other phenomena, unless such consumption or loss is at a rate that is predictable. The inert tracer(s) used in the present invention is preferably substantially unconsumed in the use environment. An inert tracer(s) that is wholly inert in the water system environment would not react with any of the component in the water of the paper system to which it is added, including the treating component(s) being used in the system, would not degrade in the environment of the water of the paper system, would be incapable of coupling and/or/ deposit in any manner within such paper system and would not appreciably be affected by other system parameters such as pH, temperature, shear, etc.

There are numerous fluorescent tracers which are capable of performance in pulp and papermaking systems and whose concentrations may be quantitatively measured at trace levels ranging from parts per trillion (ppt) to parts per million (ppm). These tracers may be chosen from classes of materials which are excited by absorption of light and produce fluorescent light emission, where the excitation and emission light occurs at any point within the far ultraviolet to near infrared spectral regions (wavelengths from 200–800 nm). Examples include, but not limited to, derivatives of fluorescein, rhodamines, naphthalenes, pyrenes, anthracenes, stilbenes, pyrazolines, courmarins, and carbostyrils. Combinations of one or more fluorescent tracers may be used in combination with other fluorescent materials as long as the absorption of excitation light and emission of fluorescent light from the other components does not interfere with detection of light emission from the fluorescent tracers.

By properly choosing the fluorescing compound, quantitative and in situ measurement of tracer levels from parts per trillion (ppt) to parts per million (ppm) can be routinely accomplished on an instant or continuous basis with inexpensive portable equipment. In addition, multiple tracers may be used concurrently by choosing tracers with proper spectral characteristics.

Some fluorescent materials may possess desirable characteristics which are preferred in certain applications. For example, rapid dissolution in water is desirable for a fluorescent tracer being employed in aqueous systems. Therefore, any material which is capable of fluorescing when dissolved or present in the performing liquid or a system or liquid employed during analytical measurement of the fluoresce emission may serve as a fluorescent tracer.

The use of fluorometry to quantitatively measure fluorescent tracers in liquid systems has special advantages compared to other trace analysis techniques as follows:

1. very good selectivity as only a very small percentage of organic compounds fluoresce to a significant extent;
2. a sufficient number of compounds are fluorescent so that, for any particular system, a tracer can be chosen for optimal performance (e.g. spectral properties, solubility, chemical inertness, low toxicity, etc.);
3. tracers can be used in a broad range of organic and inorganic liquid systems ranging from polar solvents (such as water and alcohols) to nonpolar hydrocarbon solvents;
4. very good selectivity is obtained since two spectral parameters can be varied and optimized (wavelength of light used to excite the tracer and the wavelength of fluorescence emission observed);
5. proper choice of excitation light wavelength and fluorescence emission wavelength provide ability to individually quantify one or more tracers, even in the presence of other florescent materials;
6. exceptional sensitivity with detection limits down to parts per trillion without requiring high sophisticated equipment;
7. proper choice of tracers provides very good resistance to changes in fluorescence emission due to operating conditions of the system (e.g. pH, temperature, dissolved salts, particulate matter, etc.).

Generally it is desirable to employ the least amount of tracer chemical that is practical for the circumstance, and the amount of the tracer added to the process stream should be at least an amount effective for the determinations desired. Such determinations may include, inter alia, improper dosage of treating agent, leakage in the system, improper feed point of pulp or treating agent, unbalanced pH levels, excessive dilution and improper degree of agitation. Seldom would a tracer be deliberately fed to a process stream in an amount grossly in excess of the minimum effective amount because there generally would be no practical purpose in doing so that would justify the costs involved and any deleterious effects on the quality of the paper produced caused by the presence of the tracer chemical therein. Typically, the dosage of tracer will be at least sufficient to provide a concentration of tracer within the sample of about 0.010 ppm, and more commonly at least 0.100 to 10,000 ppm.

In certain embodiments of the invention, the process includes the preliminary steps of sampling the paper process stream, preferably at all intended post-tracer-addition sampling sites, to determine baseline conditions. Such preliminary baseline condition(s) determination(s) may also be employed to narrow the selection choice of tracer chemicals or determine and/or modify the selection of post-tracer addition sampling points.

Analysis of the samples taken from the papermaking process stream may include monitoring where in the system the tracer is found, how long it takes to travel from one part of the system to another and degree of degradation of concentration, if any, experienced by the tracer at given points within the system. These and other measurements can be made in accordance with making any of the determinations discussed above and may result in a variety of solutions. Changing dosage of treating agent is an example of one such solution, but others such as plugging leaks and unclogging blocks in the system may also be appropriate depending on the type of sampling done and the results of any analysis carried out on the sample.

The following examples are presented to describe preferred embodiments and utilities of the invention and are not meant to limit the invention unless otherwise stated in the claims appended hereto.

EXAMPLE 1

Turnover Rates Of Storage Tanks Or Chests

A variety of storage tanks and holding chests are found throughout the papermaking system.(FIG. 1) The volumes of such tanks/chests can range over several orders of magnitude with the largest having tonnage capacity. Precise knowledge of turnover rates for these tanks is very important for the appropriate use of chemical additives such as biocides. A tracing agent has been used to determine turnover rates.

I. Refined Kraft Chest—Continuous Feed

Refined Kraft Chest Parameters

| TOTAL CHEST VOLUME | PUMP FLOW RATE | UTILIZED VOLUME | TURNOVER RATE (CALC.) |
|---|---|---|---|
| 19040 gal | 350 gpm | 15000 gal (80%) | 44 min |

Figure 2:
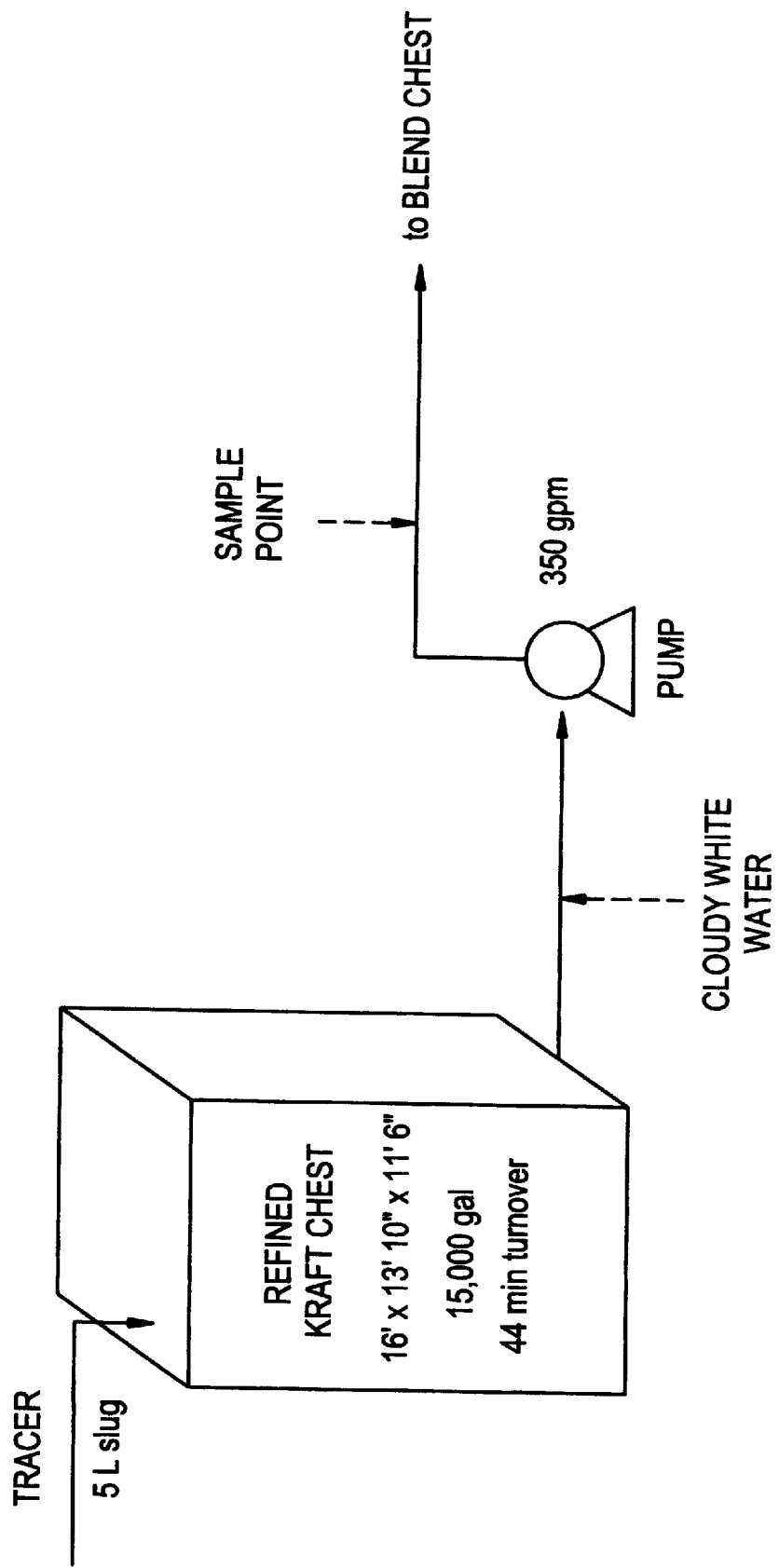
FIG. 2 is a schematic of a Minnesota paper mill's refined Kraft system.

A fluorescent tracing agent was fed into the chest continuously for approximately one hour at a rate of 22 mL/min. Stock samples were collected from the discharge of the transfer pump (after some dilution had occurred from white water, FIG. 2) every three minutes while feeding said tracing agent and for one hour after the feed had ceased. All samples were filtered through 0.45 μm Millipore® disks prior to recording fluorescence measurements.

Figure 3:
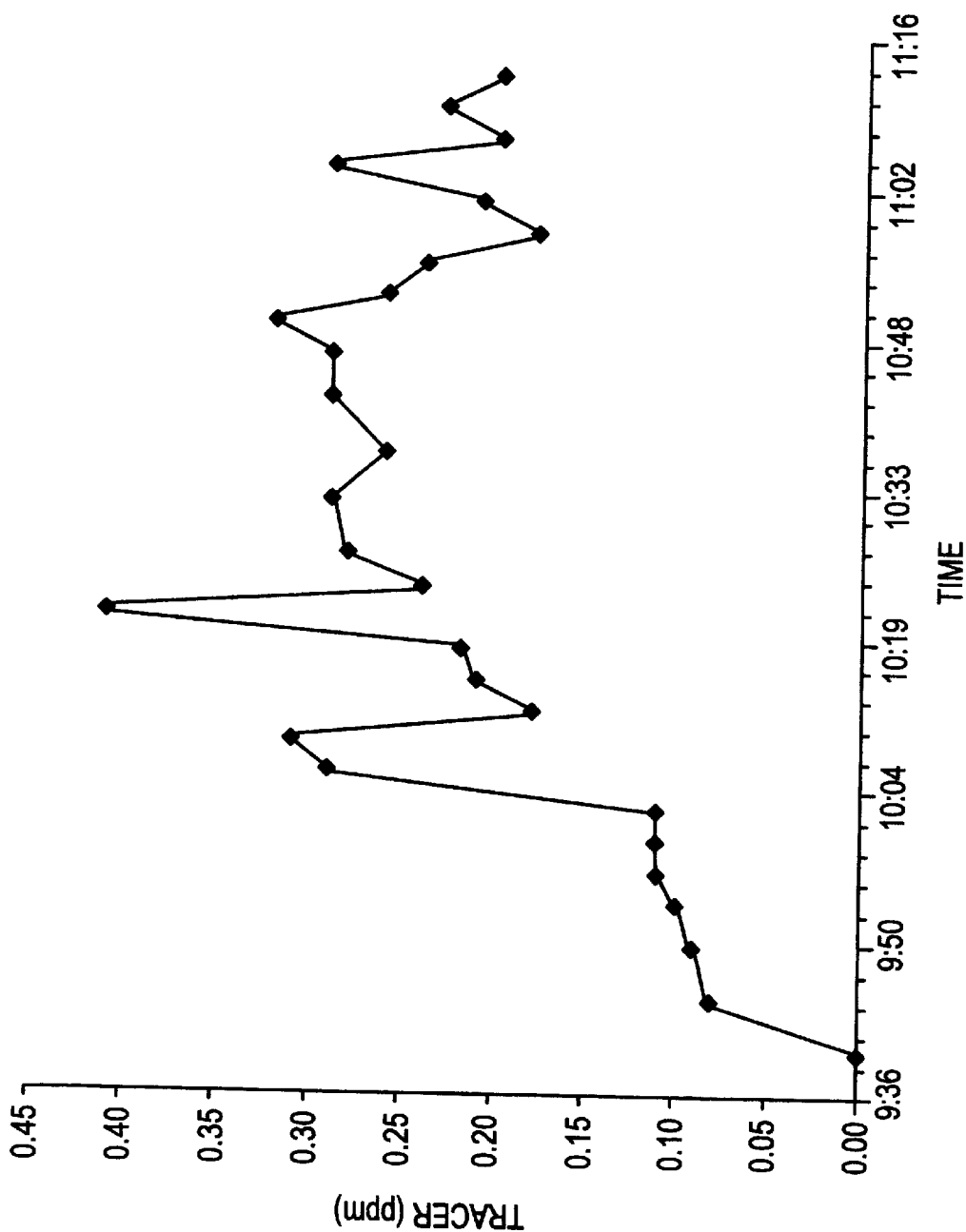
FIG. 3 is a plot of observed tracing agent fluorescence versus time for a continuously fed trail.

The plot of FIG. 3 indicates that the tracing agent was detected within 9 min after its initial feed to the Refined Kraft Chest. This is substantially less than the calculated chest turnover of 44 min indicating some degree of channelling. The fluorescence readings appear to "plateau" at about 33 min and are maintained for one hour after the fluorescent reagent addition was completed. This suggests that the system had reached a mixing equilibrium and more closely compares to the calculated 44 min chest turnover. The maximum fluorescence value of 0.410 ppm is only 30% of the theoretical level. This decrease may be a result of dilution effects, variability in the pump flow rates, or other unknown phenomena which may have occurred.

II. Refined Kraft Chest—Slug Feed

Figure 4:
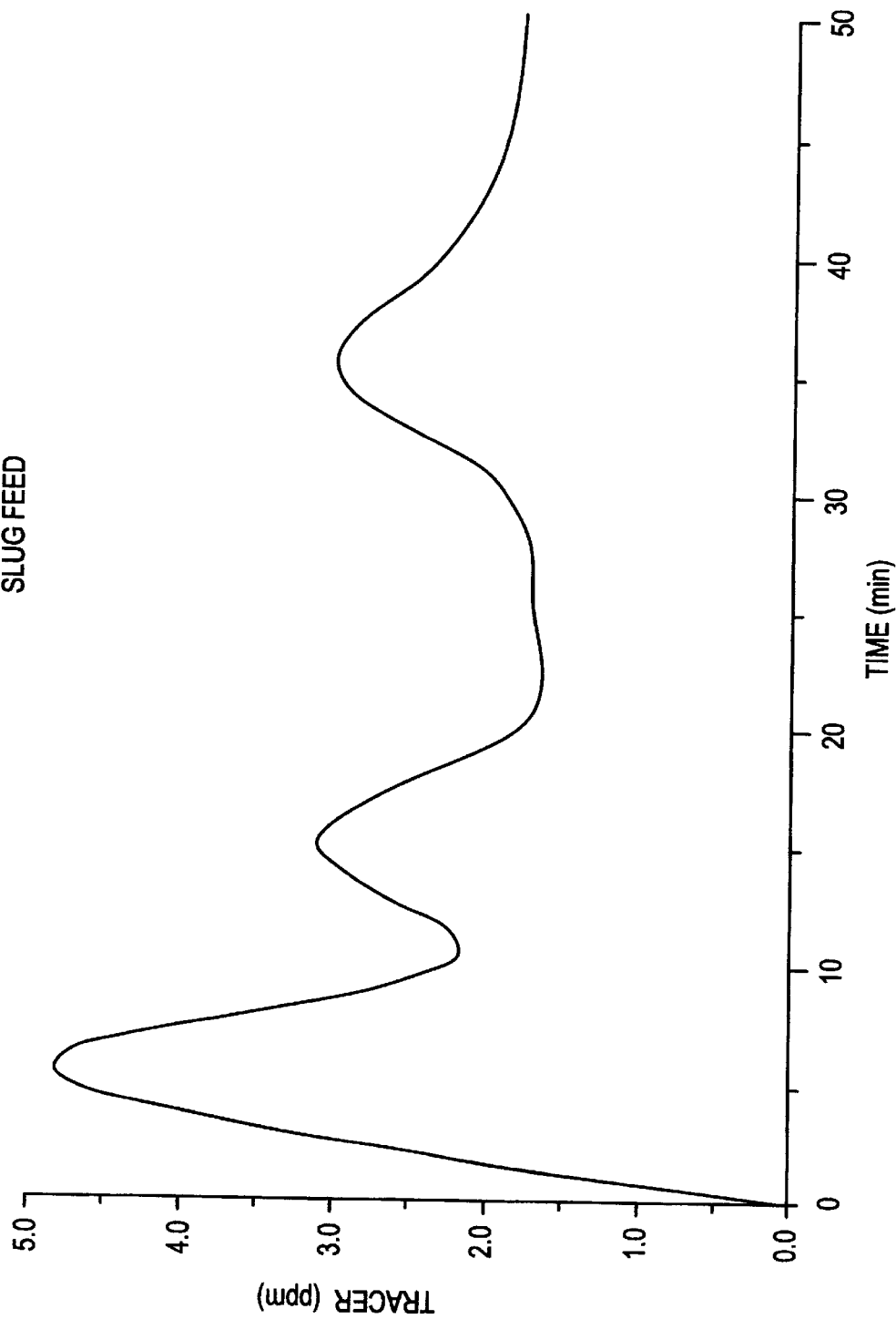
FIG. 4 is a curve of observed tracing agent fluorescence versus time for a slug fed trial.

A fluorescent tracing agent (15 gal, 10 ppm actives) was added to the Refined Kraft Chest as a "slug". Samples of furnish were collected every 5 min at the transfer pump discharge, downstream of a chest dilution site. Residual fluorescence versus time are shown in FIG. 4. The tracing agent was detected within 5 min (~5 min) after the slug was injected. This indicates that some undesirable channelling was present in the chest and is consistent with the results obtained during the continuous feed trial. Two other peaks were observed at 15 and 35 min. The former peak could be attributed to a small pocket of tracing agent that was initially stagnant in a chest dead spot and then migrates towards the suction of the transfer pump. The final peak (35 min) is closest to the calculated chest turnover of 44 min.

EXAMPLE 2

Leak Detection

Figure 5:
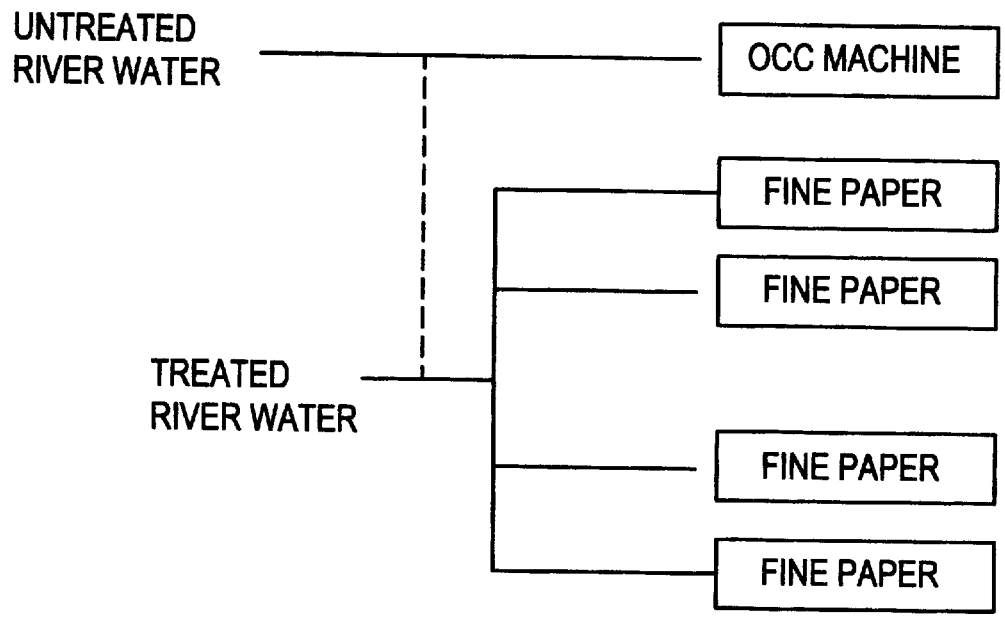
FIG. 5 is a schematic of a Wisconsin paper mill's process water system.

A Midwestern papermachine had been experiencing lower than desired felt life resulting in excessive downtime, lost production, and increased costs of felts. FIG. 5 shows a schematic of the mill's water system. The main filling component was determined to be bacteriological. Conventional approaches to felt cleaning were ineffective. Biocide batch washing was implemented, and biodispersants were evaluated but found to be only marginally effective. The mill used bleach, which controlled the microbiological problem but resulted in increased corrosion on the machine and burnt felts. Mill personnel suspected that these problems were associated with leakage of the untreated fresh water supply into the mill's process water. A tracing agent was fed into the mill's fresh water supply. Background samples (blank) were obtained for most of the sampling points prior to the addition of the tracing agent to the system. The results (see Table I; values expressed as ppm tracer) of the tracing trial confirmed the presence of fresh water leakage into the process water. The mill was able to immediately re-plumb the piping where undesirable leakage was present.

TABLE I

| Sample No. | Location | Blank | Time I | Time II | Time III |
|---|---|---|---|---|---|
|  | #15 Vac Seal Raw |  | 8.040 |  |  |
|  | Outfall of Main |  | 8.090 |  |  |
|  | RW #15 Dry End |  | 0.020 |  |  |
|  | Basement RW |  | 7.774 |  |  |
| 1 | 65 Coater HFW | 0.001 | 0.004 | 0.014 | 0.007 |
| 2 | #15 Tray | 0.006 | 0.010 | 0.010 | 0.014 |
| 3 | #15 HB Shower | 0.001 | 0.012 | 0.015 | 0.007 |
| 4 | #15 Soap Tank | 0.002 | 0.113 | 0.001 | 0.002 |
| 5 | RW Clear Sewer | 0.130 | 8.000 | 1.850 | 0.395 |
| 6 | HFW #11/15 | 0.002 | 0.020 | 0.016 | 0.007 |
| 22 | Trimbey FW | 0.001 | 0.000 | 0.000 |  |
| 23 | Starch Cooker |  | 0.014 | 0.011 | 0.007 |
| 24 | #15 Aisle Air | 0.006 | 0.009 | 0.002 |  |
| 25 | 65-1 Heat | 0.007 | 0.011 | 0.017 | 0.020 |
| 26 | #15 RP Filters | 0.008 | 0.043 | 0.007 | 0.006 |
| 27 | #15 Stock Saver | 0.006 | 0.010 | 0.005 |  |
| 28 | #15 Size Filters |  |  |  |  |
| 29 | #15 Deckle | 0.003 | 0.110 | 0.005 |  |
| 7 | #11 Felt Showers | 0.002 | 0.017 | 0.014 | 0.008 |
| 8 | #11 Tray | 0.007 | 0.008 | 0.014 | 0.017 |
| 9 | #11 HB Shower | 0.003 | 0.012 | 0.014 | 0.007 |
| 10 | #12 Tray |  | 0.006 | 0.010 | 0.012 |
| 11 | #12 HB Shower | 0.006 | 0.013 | 0.013 | 0.008 |
| 12 | #12 Knock Off |  | 0.012 | 0.011 | 0.008 |
| 30 | #12 Edge Shower | 0.003 | 0.011 | 0.018 | 0.007 |
| 31 | #11 Make-up | 0.004 | 0.002 | 0.001 |  |
| 32 | #12 Felt Shower |  | 0.013 | 0.017 | 0.008 |
| 13 | HFW at Silica | 0.003 | 0.015 | 0.015 | 0.008 |
| 17 | #14 Tray | 0.008 | 0.009 | 0.009 | 0.009 |
| 18 | #14 Deckle Shower | 0.003 | 0.010 | 0.014 |  |
| 19 | #14 Felt Shower | 0.003 | 0.012 | 0.014 | 0.008 |
| 33 | #14 Saveall | 0.007 | 0.004 | 0.008 |  |
| 34 | #14 Clarified | 0.008 | 0.005 | 0.009 |  |
| 35 | #14 Saveall | 0.010 | 0.006 | 0.009 |  |
| 15 | Tank 18 | 0.009 | 0.076 | 0.085 | 0.057 |
| 16 | Tank 22 | 0.006 | 0.009 | 0.009 |  |
| 14a | HFW Tank Feed | 0.003 | 0.002 | 0.001 |  |
| 14b | HFW Tank Feed |  | 0.000 | 0.001 |  |
| 14c | HFW Tank Feed | 0.003 | 0.001 | 0.002 |  |
| 14e | HFW Tank Feed | 0.003 | 0.001 | 0.000 |  |
| 14f | HFW Tank Feed | 0.003 | 0.002 | 0.000 |  |
| 14h | HFW Tank Feed | 0.003 | 0.000 | 0.003 |  |
| 14i | HFW Tank Feed | 0.003 | 0.000 | 0.000 |  |
| 14k | HFW Tank Feed | 0.003 | 0.015 | 0.013 | 0.007 |
| 14l | HFW Tank Feed | 0.003 | 0.002 | 0.002 |  |
| 14m | HFW Tank Feed | 0.003 | 0.054 | 0.019 | 0.005 |
| 14n | HFW Tank Feed | 0.006 | 0.007 | 0.007 |  |
| 14o | HFW Tank Feed | 0.007 | 0.006 | 0.009 |  |
| 21 | RMF HFW | 0.003 | 0.002 |  |  |
| 20 | 64-1 Coater HFW | 0.003 | 0.009 |  |  |
| 36 | #15 Saveall | 0.002 | 0.001 | 0.001 |  |
| 37 | #12 Saveall | 0.002 | 0.002 | 0.005 |  |
| 38 | #14 Saveall | 0.003 | 0.001 | 0.001 |  |

EXAMPLE 3

Additive Flows

A Midwestern paper mill was experiencing excessive corrosion in a particular process line. The mill suspected that the corrosion was related to selective channelling of chlorine dioxide in this line. A fluorescent tracing agent was added to the system to determine the flow of the chlorine dioxide.

Figure 6:
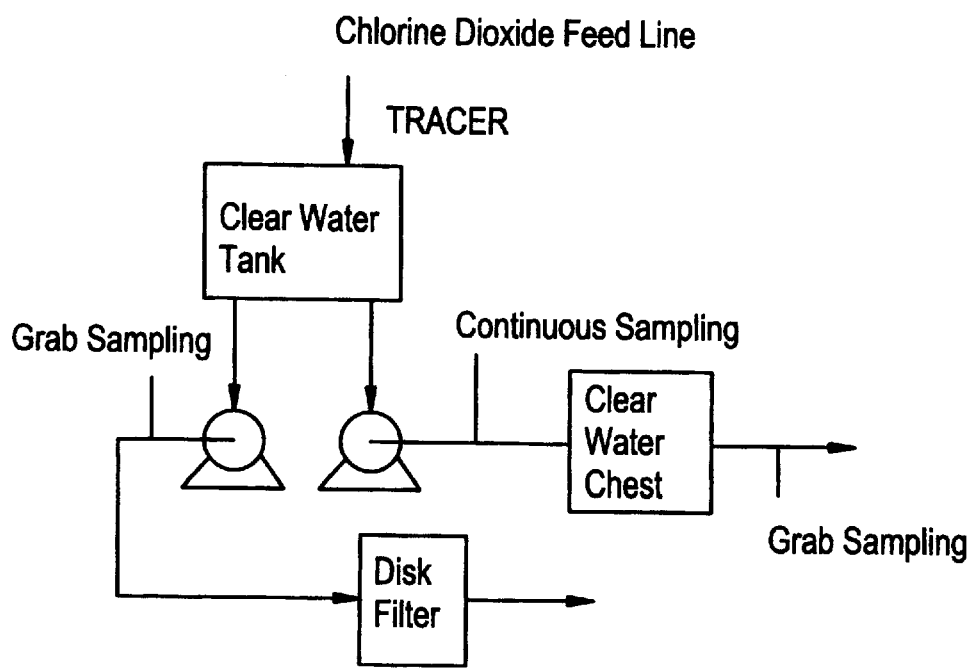
FIG. 6 is a schematic of a Midwestern paper mill's chlorine dioxide flow loop.

A schematic of the chlorine dioxide flow loop is shown in FIG. 6. The chlorine dioxide was fed into the Clear Water Tank and is then spit into two process lines—Clear Water Chest and the Disk Filter line. The Clear Water Chest process stream was experiencing excessive corrosion. A fluorescent tracing agent was added directly into the chlorine dioxide feed line prior to the Clear Water Chest. The fluorescent agent was monitored at three sampling points as illustrated in FIG. 6. A plot of tracing agent concentration for the three sites versus time is shown in FIG. 7. Both streams, the Disk Filter and the Clear Water Chest, see the fluorescent agent at approximately the same time suggesting that there is no unusual channelling of chlorine dioxide to the Clear Water Chest. However, there was an observable difference in fluorescence for the two streams, and presumably chlorine dioxide concentration, which could in fact cause the increase in corrosion observed in the Clear Water Chest process stream.

Changes can be made in the composition, operation and arrangement of the method of the present invention described herein without departing from the concept and scope of the invention as defined in the following claims:

I claim:

1. A method of tracking the presence of a treating component in a papermaking system, wherein said treating component is chlorine dioxide and wherein said papermaking system comprises:

i) a clear water tank;
   ii) a clear water chest; and a
   iii) disk filter;
   wherein said chlorine dioxide is pumped to said clear water tank through a chlorine dioxide feed line; and
   there are at least two exit lines from said clear water tank;
   wherein the first of said exit lines from said clear water tank is also the inlet line to said disk filter and the second of said exit lines from said clear water tank is also the inlet line to said clear water chest; and
   wherein there is an exit line from said disk filter and an exit line from said clear water chest;
   comprising the steps of:

a) adding to said chlorine dioxide feed line an inert water soluble fluorescent tracer in an amount proportional to the amount of chlorine dioxide in said chlorine dioxide feed line to create a standard amount of detectable fluorescence in said chlorine dioxide feed line;
   wherein said tracer is selected from the group consisting of derivatives of rhodamines, pyrenes, anthracenes, stilbenes, pyrazolines, coumarins, and carbostyrils, and wherein said tracer remains physically and chemically separate from the chlorine dioxide;
   b) withdrawing from the system a sample solution containing said tracer at sampling points, wherein there are at least three sampling points in said papermaking system, with the first sampling point being in the first exit line from said clear water tank, the second sampling point being in the second exit line from said clear water tank and the third sampling point being in the exit line from said clear water chest;
   c) conducting a fluorometric analysis of said sample solution by using a fluorometer to detect the amount of fluorescence in said sample solution and comparing the amount of fluorescence detected to the standard amount of detectable fluorescence known in step A) to determine the concentration of chlorine dioxide in the sample; and
   d) adjusting one or more variables in the papermaking system to maintain said chlorine dioxide at a desired level.

* * * * *